US00PP33192P2

(12) United States Plant Patent
Hansen

(10) Patent No.: US PP33,192 P2
(45) Date of Patent: Jun. 22, 2021

(54) ***AGAVE* PLANT NAMED 'SABERTOOTH TIGER'**

(50) Latin Name: ***Agave titanota* Gentry**
Varietal Denomination: Sabertooth Tiger

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,409

(22) Filed: Jan. 19, 2021

(51) Int. Cl.
*A01H 6/12* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique *Agave* plant named 'Sabertooth Tiger' characterized by dense, low, mounded plant habit of short, obovate, variegated leaves having wide creamy-white centers with green margins. The leaves have firm, sharp large-sized marginal teeth positioned on the distal apical region and show occasional imprints from marginal spines of leaves above or below. The marginal teeth curve upwardly and toward shoot apex. The apical spine is long, firm and sharp. The plant is useful in the landscape as a specimen, en masse, or also in a container in the home or landscape.

2 Drawing Sheets

Botanical classification: *Agave titanota* Gentry.
Variety denomination: 'Sabertooth Tiger'.

BACKGROUND OF THE INVENTION

The present invention relates to the new and distinct *Agave* plant, *Agave* 'Sabertooth Tiger' discovered by the inventor at a wholesale perennial nursery in Zeeland, Mich., USA as an uninduced whole-plant mutation from a tissue cultured crop of *Agave* 'MSWNStarr1' (not patented) on Mar. 21, 2019. Prior to assigning the new plant a cultivar name, the new plant was identified through the evaluation process with the code 19-SP-AGAV-813. The new plant has been successfully asexually propagated by shoot tip tissue culture at a wholesale perennial nursery in Zeeland, Mich. Shoot tip tissue culture propagation has been found produce stable and identical plants that maintain the unique characteristics of the original plant.

No plants of *Agave* 'Sabertooth Tiger' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

*Agave* 'Sabertooth Tiger' is a sport of 'MSWNStarr1' which is a selection of *Agave titanota*. 'Sabertooth Tiger' differs from its parent as well as all other *Agaves* known to the applicant. The most similar known *Agave* cultivars other than the parent are *Agave isthmensis* 'El Chichon' (not patented), 'Kissho Kan Nishiki' (not patented), *A. potatorum* 'Becky' (not patented), *Agave titanota* 'X-Rays' (not patented), *Agave titanota* 'Medioaurea' (not patented), *Agave titanota* 'Genyru' (not patented) and *Agave titanota* 'Miracolo' (not patented). 'El Chichon' has much smaller habit and foliage that is less obtuse and more deltoid, the variegation coloration is similar but the marginal teeth are smaller and less curved. 'Kissho Kan Nishiki' has leaf centers are noticeably more chartreuse and smaller marginal teeth. 'Becky' has foliage that is more glaucous, and the white center variegation has more greenish blush. 'X-Rays' has a much larger habit, the leaves are more glaucous and the muted, creamy-white, central band is much narrower. 'Medioaurea' has a center variegation that is more chartreuse as it emerges and becomes more medium green with age. 'Genryu' has a larger habit with more lanceolate leaves and the green margin is narrower. 'Miracolo' has a larger habit with more lanceolate concave leaves and the center is more creamy yellow.

'MSWNStarr1' has a similar habit and leaf shape, but the variegation pattern is reversed with the creamy-white being on the margin and the green in the center. The parent also has a more noticeable intermediate zone of whitish-green between the margin and center variegation.

*Agave* 'Sabertooth Tiger' differs from all other *Agaves* known to the applicant, by the combination of the following traits:

1. Short, obovate, thick, variegated leaves with marginal teeth and apical spine;
2. Leaves have wide green margins and contrasting creamy-white leaf centers;
3. Large, firm, sharp, marginal teeth are positioned only on the distal region and not on the proximal leaf sides;
4. Marginal teeth tend to curve upward and toward shoot apex;
5. Apical spines are long, firm and sharp;
6. Marginal teeth leave an imprint on the underside of distal leaves;
7. Habit is low mounded with mostly outright to horizontal foliage.

BRIEF DESCRIPTION OF THE DRAWINGS

The photograph of the new plant demonstrates the overall appearance of the new plant including the unique traits as a one-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
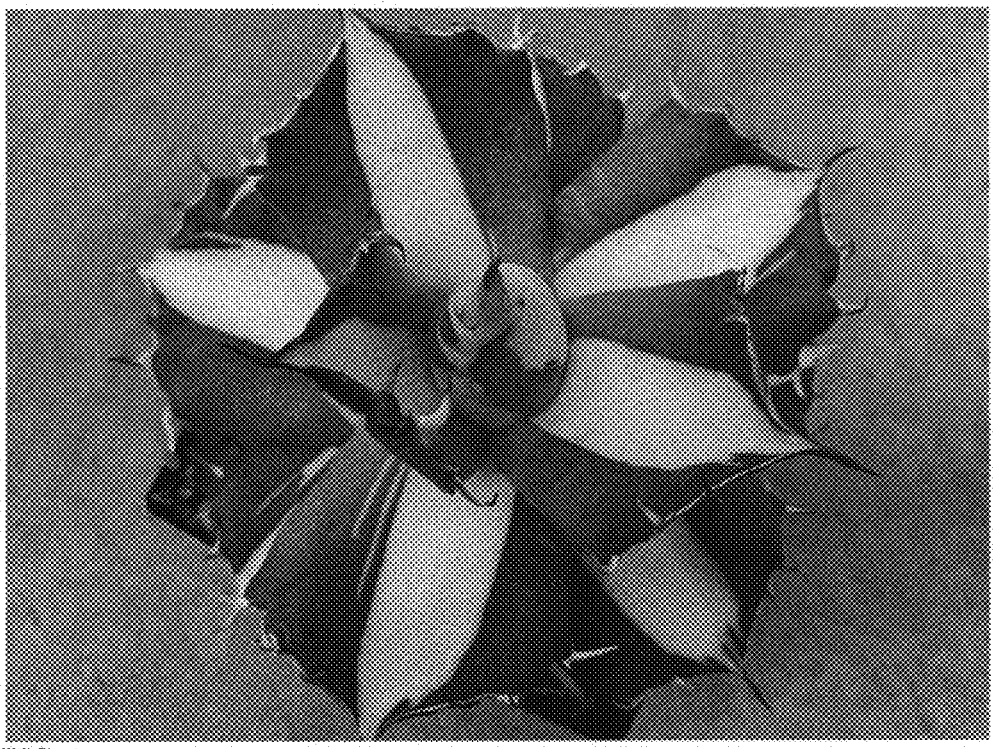
FIG. 1 shows a top view of the new plant in a container with new unfurling foliage and marginal teeth and apical spines.
Figure 2:
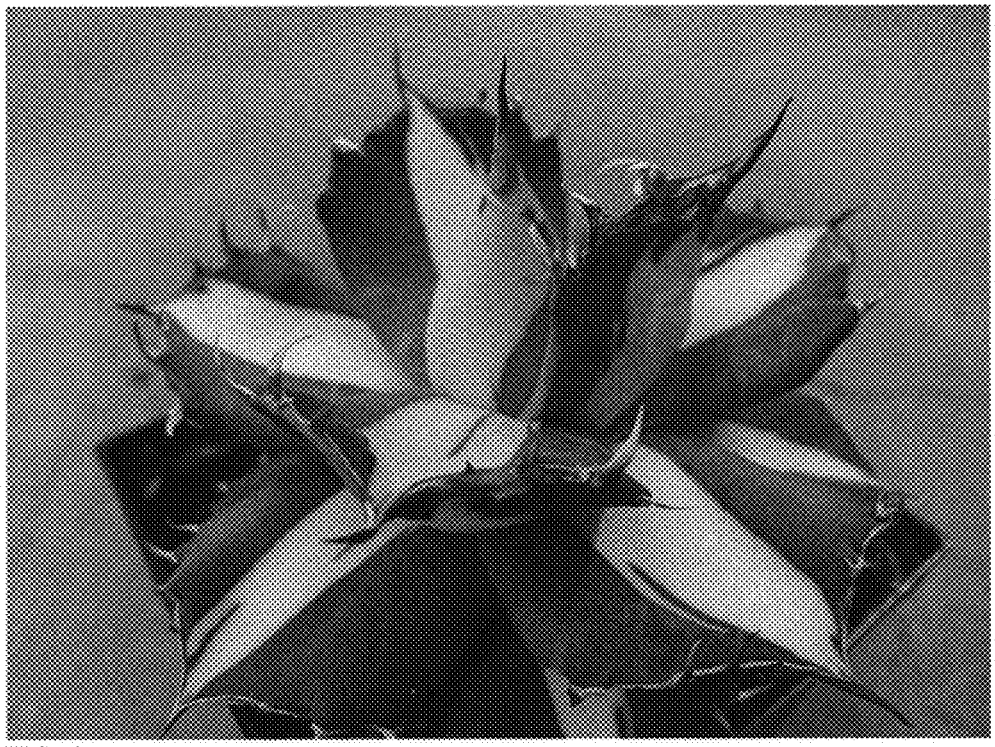
FIG. 2 shows a side view of the new plant in a container.
Figure 3:
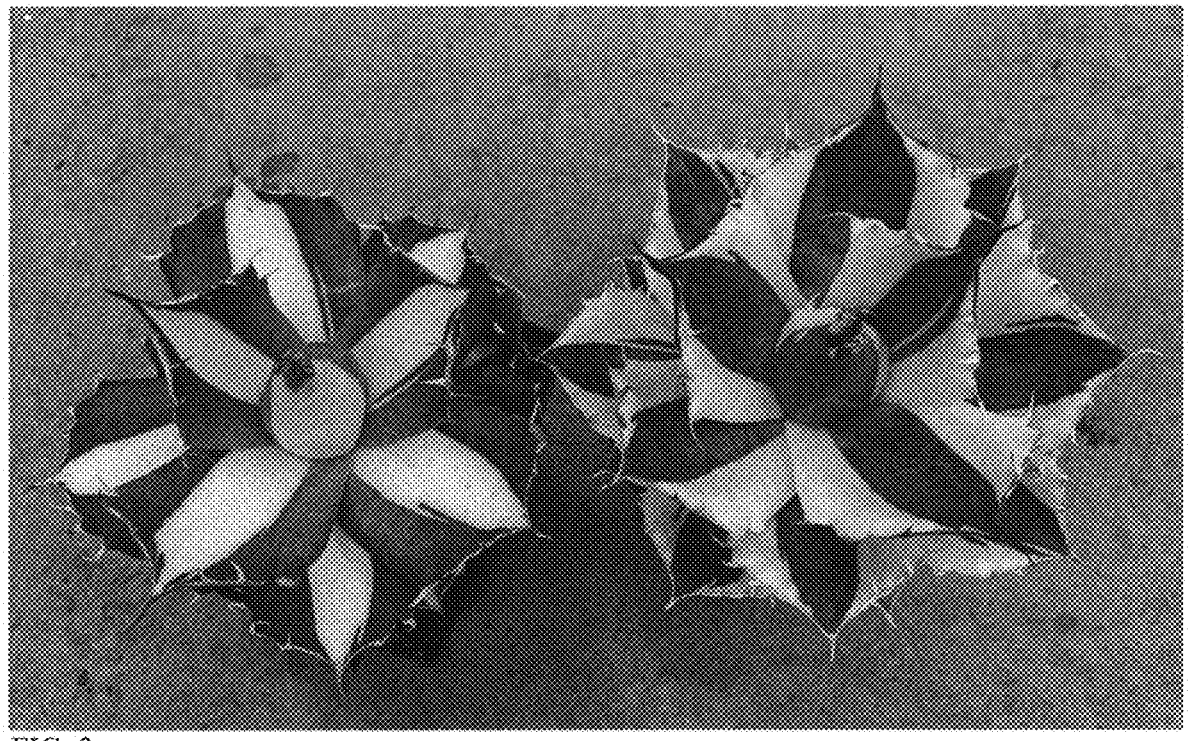
FIG. 3 shows a comparison of the 'MSWNStarr1' (on the right) with the new plant (on the left).

The following descriptions and color references are based on the 2015 edition of The Royal Horticultural Society Colour Chart except where common dictionary terms are used. The new plant, *Agave* 'Sabertooth Tiger', has not been observed under all possible environments. The phenotype may vary slightly with different environmental conditions, such as temperature, light, fertility, moisture and maturity levels, but without any change in the genotype. The following observations and size descriptions are of a one-year-old plant in a commercial wholesale greenhouse in Zeeland, Mich. with supplemental water and fertilizer as needed.

Botanical classification: *Agave titanota;*

Variety denomination: 'Sabertooth Tiger';

Sport parentage: Uninduced whole-plant sport of *Agave* 'MSWNStarr1';

Propagation: Shoot tip tissue culture;

Time to initiate roots: About 30 days;

Growth rate: Moderate to slow;

Crop time: About 12 months to finish in a 3.8 liter container from an established offset;

Rooting habit: Fleshy, lightly branching, with roots up to 12 cm long;

Root color: Nearest RHS NN155B;

Plant shape and habit: Herbaceous tender perennial with basal rosettes of broad, variegated, densely whorled leaves emerging from central base, producing a low dense symmetrical mound;

Plant size: Foliage height about 12.0 cm tall from soil line to the top of the leaves and about 14.0 cm wide at the widest point slightly above soil line when grown in containers;

Stem: Compressed; about 3.0 cm long; completely covered with leaves;

Foliage description: Obovate; simple; sarcous; abruptly acute apex ending in medium-length stiff spine; truncate sessile base; marginal, upwardly and backwardly-pointing, sharp, stiff spines in distal portion; glabrous, scabrous and slightly glaucous adaxial and abaxial; attitude mostly outwardly;

Number of leaves: About 25 per plant;

Leaf size: To about 6.8 cm long, 5.0 cm wide near apex, 3.8 cm wide near base and 1.0 cm thick near base; average 6.5 cm long, 4.5 cm wide near apex, 3.6 cm wide at base and 0.8 mm thick near base;

Leaf variegation dimensions: Adaxial margin to 20.0 mm wide near apex and tapering to about 10.0 mm near apex; abaxial margin to about 13.0 mm near apex and tapering to about 7.0 mm wide at base; adaxial and abaxial intermediate zone not apparent at one-year of age; adaxial center to about 22.0 mm wide near middle; abaxial center to about 33.0 mm cm wide near middle; with irregular narrow longitudinal stripes of green extending various random lengths into the creamy-white center zone and narrow creamy-white longitudinal stripes of various random lengths extending into the green margins of mostly on adaxial and rarely on abaxial;

Foliage fragrance: None observed;

Leaf blade color:

*Expanding young adaxial.*—Margin a blend between RHS 138A and RHS 146B, center variable between nearest RHS 4D distally and proximally between RHS 4D and RHS 155A.

*Expanding young abaxial.*—Margin a blend between RHS 138A and RHS 146B, center variable between nearest RHS 4D distally and proximally between RHS 4D and RHS 155A.

*Mature adaxial.*—Margin nearest RHS NN137A with slight glaucous bloom nearest RHS N138C, center nearest a blend between RHS 4D and RHS 155A.

*Mature abaxial.*—Margin nearest RHS NN137C with slight glaucous bloom nearest RHS N138C, center nearest a blend between RHS 4D and RHS 155A.

Apical spine: Stiff and sharp; to about 10.0 mm long, about 1.0 mm across at base;

Apical spine color: Between RHS N199A and RHS 200A;

Marginal teeth: Sharply pointed; typically three on each side on apical portion only; stiff; pointing upwardly and slightly curved toward shoot apex; to about 9.0 mm long and about 3.0 mm wide at base; average about 10.0 mm apart;

Marginal teeth color: On young emerging and mature leaves a blend of nearest RHS 156C and RHS 158B;

Petiole: Sessile;

Veins: Absent;

Flower description: Flowers have not yet been observed;

Fruit and seed: Have not yet been observed;

Disease resistance: *Agave* 'Sabertooth Tiger' has not been observed to be resistant to diseases common to *Agaves* beyond that which is normal for *Agave*. The plant is xeromorphic and survives well with minimal water once established. Hardy in frost-free areas. Full extent of winter hardiness has not been tested.

I claim:

1. A new and distinct cultivar of ornamental *Agave* plant named 'Sabertooth Tiger' as herein described and illustrated.

* * * * *